United States Patent [19]
Blanch

[11] Patent Number: 4,730,498
[45] Date of Patent: Mar. 15, 1988

[54] FIXTURE FOR HOLDING A BENDING TEST SPECIMEN

[75] Inventor: John F. Blanch, Mantoloking, N.J.

[73] Assignee: Rheometrics, Inc., Piscataway, N.J.

[21] Appl. No.: 55,920

[22] Filed: Jun. 1, 1987

[51] Int. Cl.⁴ .............................................. G01N 3/20
[52] U.S. Cl. ...................................... 73/852; 73/856
[58] Field of Search ................... 73/849, 851, 852, 856

[56] References Cited

U.S. PATENT DOCUMENTS 3,937,072  2/1976  Huydts et al. ...................... 73/852

Primary Examiner—Jerry W. Myracle
Attorney, Agent, or Firm—Samuelson & Jacob

[57] ABSTRACT

A test fixture for use in measuring the forces required to bend a test specimen throughout a range of temperatures includes clamps for gripping the ends of the test specimen while bending forces are applied intermediate the ends of the specimen, the clamps being carried by carriages movable in directions aligned with the test specimen and biased away from one another by constant force springs so that movement of the ends of the test specimen is permitted in response to temperature changes in the test specimen, against the constant bias of the constant force springs, thereby maintaining the test specimen in constant tension during the measurement of bending forces despite the changes in temperature.

8 Claims, 3 Drawing Figures

FIXTURE FOR HOLDING A BENDING TEST SPECIMEN

The present invention relates generally to the mechanical testing of materials and pertains, more specifically, to a fixture for holding a test specimen to be subjected to bending while exposed to a range of temperatures.

The increased demand for more and varied materials tailored for specific end uses has led to the requirement for materials testing techniques and apparatus developed to meet the need for greater accuracy in measuring the effects of particular stresses upon a test specimen of any one of a variety of materials, such as plastics, ceramics and composites, under various ambient conditions. In particular, when measuring bending forces in a test specimen of relatively thin cross-section subjected to temperature changes, it becomes necessary to reduce to a minimum the effects of temperature changes in the test specimen during the application of a bending load.

The present invention provides a fixture which holds a test specimen in such a way as to maintain a constant tension in the test specimen during the application of a bending load, despite temperature changes in the test specimen. Accordingly, the present invention provides a fixture for holding a test specimen to be subjected to bending, which fixture exhibits several objects and advantages, some of which may be summarized as follows: The maintenance of a constant tension in a test specimen gripped adjacent the opposite ends thereof during the application of bending loads intermediate the opposite ends for enabling accurate measurement of the bending forces despite changes in the temperature of the test specimen; instantaneous accommodation of variations in the temperature of the test specimen without affecting the maintenance of constant tension in the test specimen; reliable operation over a range of operating conditions, including variations in temperature in the testing environment; operation independent of gravitational forces, enabling versatility in installation and use; simplicity of construction and use; and rugged construction for reliable use over a long service life.

The above objects and advantages, an well as further objects and advantages, are attained by the present invention which may be described briefly as a fixture for holding a longitudinally elongate test specimen gripped adjacent the opposite ends thereof and subjected to bending by the application of lateral forces at a location intermediate the opposite ends, while maintaining a constant tension in the test specimen along the longitudinal direction despite temperature changes in the test specimen throughout a range of temperature and consequent longitudinal displacement of the opposite ends thereof, the fixture comprising: a pair of longitudinally spaced apart gripping means for gripping the respective opposite ends of the test specimen; at least one, and preferably a pair of carriages, each carriage carrying one of the gripping means, the carriages being movable in longitudinal directions toward and away from one another over a range of movement; a constant-bias device coupled to each one of the carriages so as to bias the carriages in the direction away from one another with a constant biasing force throughout the range of movement of the carriages, such that the constant biasing force will maintain the constant tension in the test specimen despite temperature changes in the test specimen throughout the range of temperature and consequent longitudinal displacement of the opposite ends thereof.

The invention will be understood more fully, while still further objects and advantages will become apparent in the following detailed description of a preferred embodiment of the invention illustrated in the accompanying drawing, in which.

Figure 1:
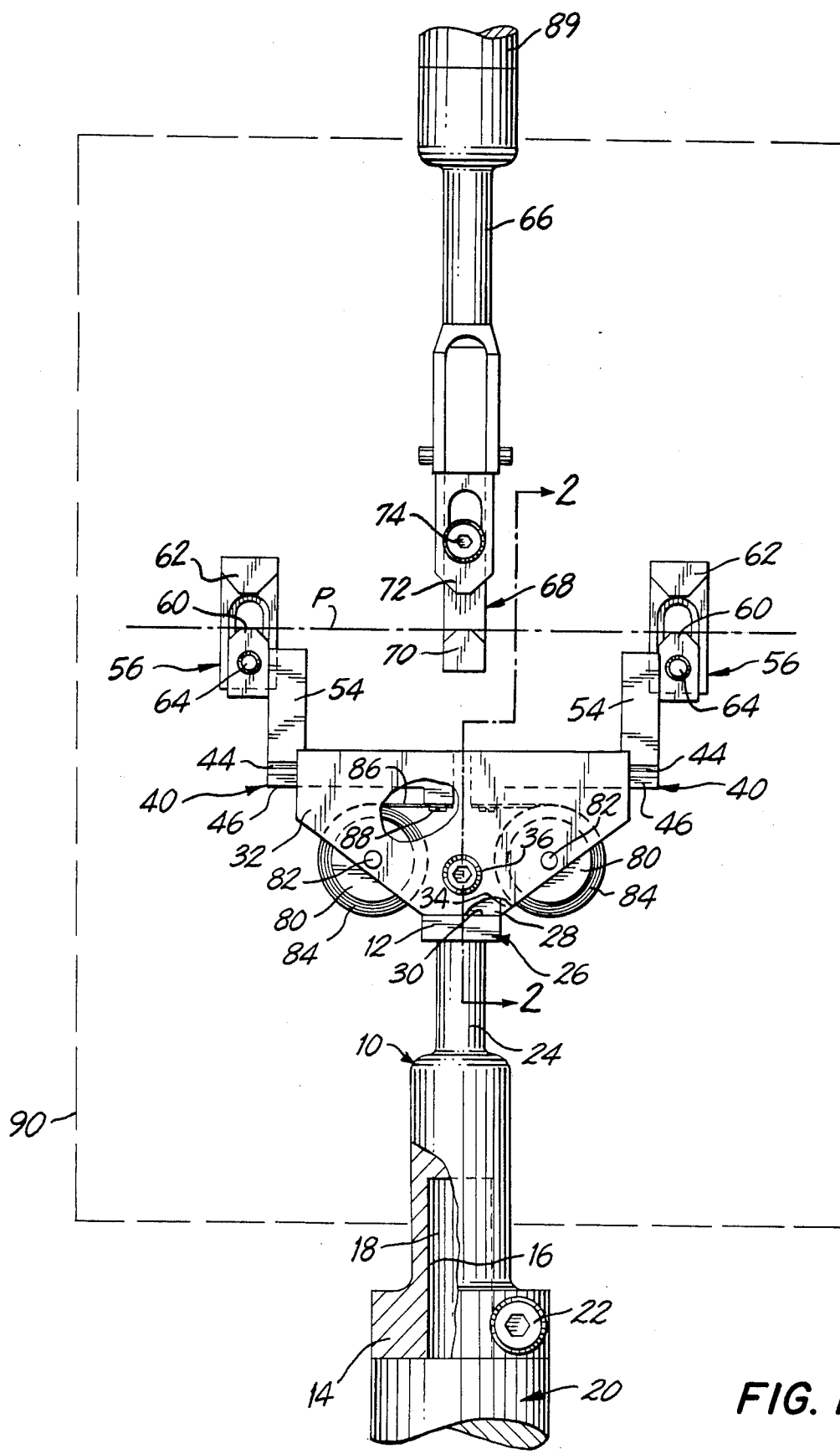
FIG. 1 is a front elevational view of a fixture constructed in accordance with the invention.
Figure 2:
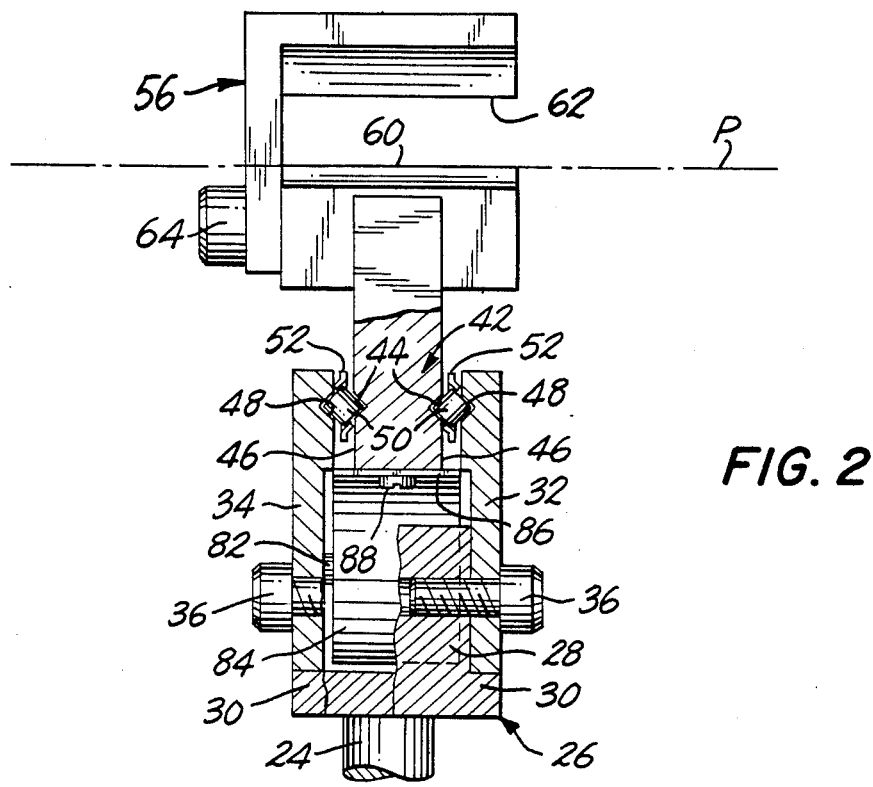
FIG. 2 is an enlarged cross-sectional view taken along line 2—2 of FIG. 1.

Referring now to the drawing, and especially to FIGS. 1 and 2 thereof, a fixture constructed in accordance with the invention is shown at 10 and is seen to include a frame 12 having a base 14 with a socket 16 for receiving a complementary mounting spindle 18 of the testing machine 20 in connection with which fixture 10 is to be utilized. A clamping screw 22 secures the base 14 to the spindle 18. A pedestal 24 extends upwardly from base 14 and carries a mounting bracket 26 having an upwardly-extending central block 28 and a flange 30 projecting laterally at each side of the mounting bracket 26. A front plate 32 and a rear plate 34 each rest upon a corresponding flange 30 and threaded fasteners 36 extend through each plate 32 and 34 adjacent the lower edge thereof and secure the plates 32 and 34 to block 28, in place on bracket 26.

A pair of carriages 40 are placed between plates 32 and 34 adjacent the upper edges of the plates, the carriages 40 being mounted within a guideway 42 between the plates 32 and 34 for linear movement in longitudinal directions toward and away from one another. Thus, each carriage 40 has a pair of V-shaped grooves 44 extending longitudinally along the sides 46 of the carriage, and each plate 32 and 34 has a corresponding V-shaped groove 48 confronting a groove 44. A plurality of bearing elements in the form of canted rollers 50 are placed within the race established by the confronting grooves 44 and 48 and provide a linear bearing for facilitating linear movement of the carriages 40 toward and away from one another. A cage 52 holds the rollers 50 appropriately spaced apart along the length of the race.

Each carriage 40 includes a post 54 located at the outer end of the carriage and each post 54 carries a clamp 56 spaced upwardly away from the carriages 40 and the plates 32 and 34. Each clamp 56 includes a fixed lower jaw 60 and a movable upper jaw 62, the upper jaw 62 being held in place by a clamp screw 64. Lower jaws 60 define a plane P within which a test specimen is to be placed for bending tests, as will be explained below. Suffice it to say at this point that the test specimen spans the space between clamps 56 and is held in place for the application of bending forces at rod 66 of testing machine 20. Rod 66 carries a further clamp 68 having a fixed lower jaw 70 and a movable upper jaw 72 secured in place by a clamp screw 74. Lower jaw 70 is aligned with plane P to accept the test specimen in preparation for testing.

A drum 80, located beneath each carriage 40, is rotatable upon an axle 82 mounted between plates 32 and 34 below carriages 40. Each drum 80 carries a constant force extension spring 84 coiled around the drum 80 and having an extension 86 extending parallel to the direction of movement of the carriages 40. Each extension 86 is affixed to a corresponding carriage 40 by a fastener 88 so that carriages 40 are biased outwardly away from one another by the force of the springs 84.

Figure 3:
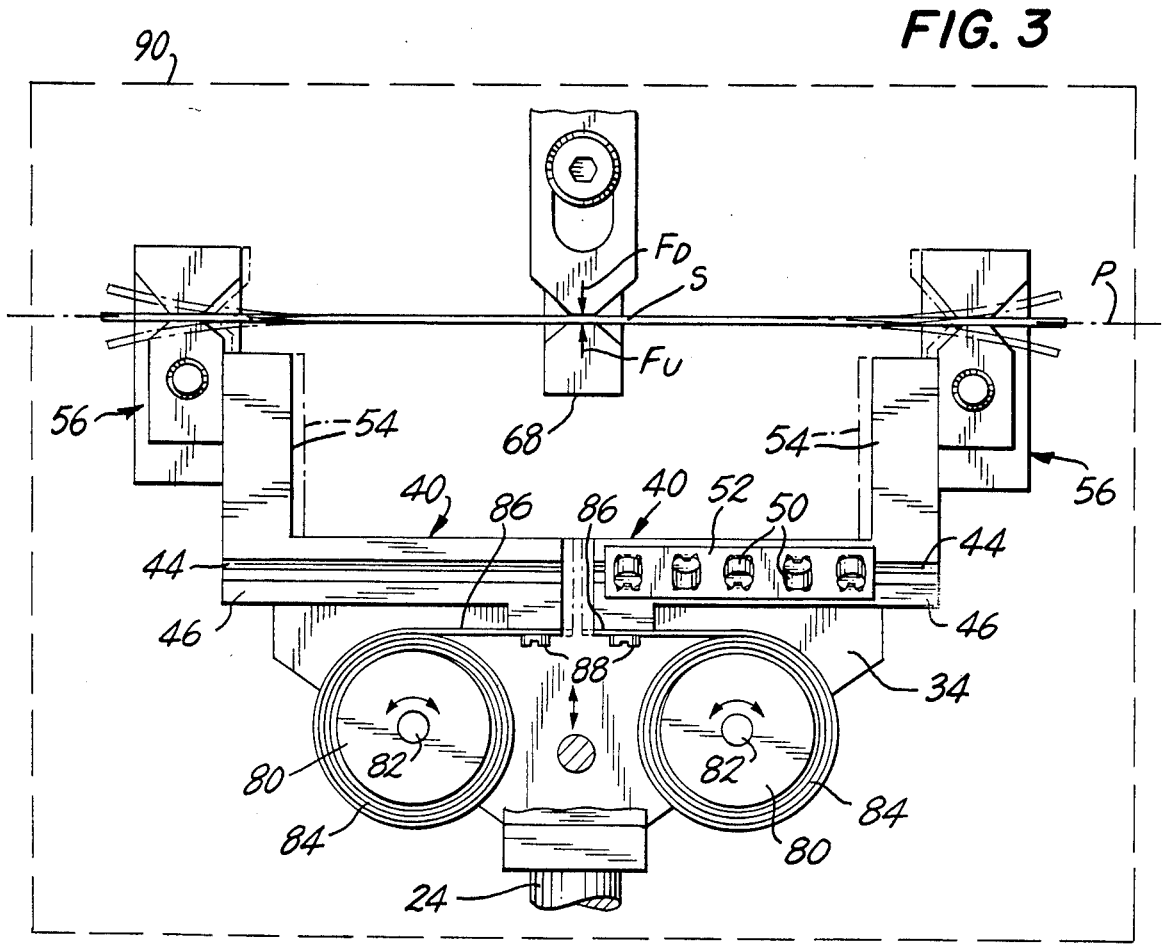
FIG. 3 is an enlarged diagrammatic illustration demonstrating operation of the fixture.

Turning now to FIG. 3, during use of the fixture 10, a test specimen S in the form of a relatively thin elongate strip of material is placed in plane P and is clamped adjacent the ends thereof in clamps 56. Clamp 68, which is located centrally intermediate the clamps 56, is clamped to the test specimen S intermediate the ends thereof. Upon downward or upward movement of the spindle 18 of test machine 20, while rod 66 remains stationary, corresponding bending forces $F_D$ and $F_U$ will be exerted upon the test specimen S, bending the test specimen S, as indicated in phantom. Bending forces $F_D$ and $F_U$ are detected by a transducer 89 coupled to rod 66. Test specimen S and at least portions of the fixture 10 are enclosed within a chamber, shown only diagrammatically at 90, so that the temperature within the chamber 90 may be varied for subjecting the test specimen S and component parts of the fixture 10 to a range of temperature during the application of bending forces $F_D$ and $F_U$. In this manner, the test specimen S can be subjected to temperatures within the range of about $-190°$ C. to $+600°$ C. while bending forces $F_D$ and $F_U$ are applied to the test specimen S. Such variations in temperature ordinarily would tend to vary the tension in the test specimen S as a result of contraction and expansion of the test specimen S and the enclosed component parts of the fixture 10; however, test specimen S is clamped adjacent the ends thereof by clamps 56 carried by carriages 40 which are movable toward and away from one another and are biased away from one another by constant force springs 84. Thus, variations in the temperature of the test specimen S will result in movement of the opposite ends of the test specimen toward or away from one another, such movement being permitted by displacement of the carriages 40 against the biasing force of springs 84. Since the ends of the test specimen S are allowed to be displaced longitudinally in response to temperature changes in the test specimen, the tension within test specimen S remains constant throughout all bending of the test specimen and the forces $F_D$ and $F_U$ are an accurate measure of the forces required solely to bend test specimen S. Moreover, the constant tension is maintained relatively low. The relatively low, constant tension enables accuracy since the measured bending forces vary with tension in the test specimen and constant tension eliminates that variable. The axles 82 and drums 80 are located relative to carriages 40 so that the springs 84 always are extended beyond the initial deflection required to place the springs 84 in the rated load configuration and the displacement of carriages 40 during bending tests is very small compared to the length of test specimen S so that the springs 84 always are operated at the rated load throughout the range of movement of the carriages 40. For example, during the testing of a typical test specimen S of plastic having a length of 1.750 inches and a thickness of 0.125 inch, and having a coefficient of thermal expansion of about $7 \times 10^{-5}$ per degree C, per inch, the displacement of each carriage 40, over a temperature range of about 790° C. will be about 0.040 inch.

It will be seen that fixture 10 has relatively few component parts, and all of the component parts are of rugged construction, preferably of stainless steel, for withstanding all of the conditions encountered during use. In particular, the use of constant force springs 84 renders the operation reliable, even under the varied temperature conditions encountered in the testing environment.

It is to be understood that the above detailed description of an embodiment of the invention is provided by way of example only. Various details of design and construction may be modified without departing from the true spirit and scope of the invention as set forth in the appended claims.

The embodiments of the invention in which an exclusive property of privilege is claimed are defined as follows:

1. A fixture for holding a longitudinally elongate test specimen gripped adjacent the opposite ends thereof and subjected to bending by the application of lateral forces at a location intermediate the opposite ends, while maintaining a constant tension in the test specimen along the longitudinal direction, despite temperature changes in the test specimen throughout a range of temperature and consequent longitudinal displacement of the opposite ends thereof, the fixture comprising:
   a pair of longitudinally spaced apart gripping means for gripping the respective opposite ends of the test specimen;
   a pair of carriages, each carriage carrying one of the gripping means, the carriages being movable in longitudinal directions toward and away from one another over a range of movement; and
   a pair of constant-bias devices, one of said devices coupled to each of the carriages so as to bias the carriages in the direction away from one another with a constant biasing force throughout the range of movement of the carriages, such that the constant biasing force will maintain the constant tension in the test specimen despite temperature changes in the test specimen throughout the range of temperature and consequent longitudinal displacement of the opposite ends thereof.

2. The invention of claim 1 wherein the constant-bias devices include constant force springs mounted for operation at the rated load thereof throughout the range of temperature of the test specimen and the range of movement of the carriages.

3. The invention of claim 2 wherein:
   the fixture includes a frame having a longitudinal guideway;
   the carriages are placed within the guideway for linear movement along the guideway; and
   linear bearing means are located between the carriages and the frame for facilitating the linear movement of the carriages within the guideway throughout the range of temperature of the test specimen and the range of movement of the carriages.

4. The invention of claim 3 wherein the constant force springs are mounted upon the frame in juxtaposition with the guideway.

5. A fixture for holding a longitudinally elongate test specimen gripped adjacent the opposite ends thereof and subjected to bending by the application of lateral forces while maintaining a constant tension in the test specimen along the longitudinal direction, despite temperature changes in the test specimen throughout a range of temperature and consequent relative longitudinal displacement of the opposite ends thereof, the fixture comprising:
   a pair of longitudinally spaced apart gripping means for gripping the respective opposite ends of the test specimen;

at least one carriage, the carriage carrying one of the gripping means and being movable in longitudinal directions toward and away from the other gripping means over a range of movement; and a constant-bias device coupled to the carriage so as to bias the carriage and the one gripping means in the direction away from the other gripping means with a constant biasing force throughout the range of movement of the carriage, such that the constant biasing force will maintain the constant tension in the test specimen despite temperature changes in the test specimen throughout the range of temperature and consequent relative longitudinal displacement of the opposite ends thereof.

6. The invention of claim 5 wherein the constant-bias device includes a constant force spring mounted for operation at the rated load thereof throughout the range of temperature of the test specimen and the range of movement of the carriage.

7. The invention of claim 6 wherein:

the fixture includes a frame having a longitudinal guideway;

the carriage is placed within the guideway for linear movement along the guideway; and linear bearing means are located between the carriage and the frame for facilitating the linear movement of the carriage within the guideway throughout the range of temperature of the test specimen and the range of movement of the carriage.

8. The invention of claim 7 wherein the constant force spring is mounted upon the frame in juxtaposition with the guideway.

* * * * *